United States Patent [19]

Roselle et al.

[11] Patent Number: 5,244,593

[45] Date of Patent: Sep. 14, 1993

[54] COLORLESS DETERGENT COMPOSITIONS WITH ENHANCED STABILITY

[75] Inventors: Brian J. Roselle, Fairfield; Donald T. Speckman, Cincinnati, both of Ohio

[73] Assignee: The Procter & Gamble Company, Cincinnati, Ohio

[21] Appl. No.: 819,050

[22] Filed: Jan. 10, 1992

[51] Int. Cl.$^5$ .......................... C11D 1/02; C11D 1/66; C11D 3/395; C11D 10/02

[52] U.S. Cl. ......................................... 252/99; 252/95; 252/102; 252/550; 252/554; 252/558; 252/174.21; 252/551; 252/100; 252/546; 252/174.19; 252/Dig. 14

[58] Field of Search ................. 252/95, 99, 102, 550, 252/554, 558, 174.21, 551, 100, 546, 174.19, DIG. 14

[56] References Cited

U.S. PATENT DOCUMENTS

| | | | |
|---|---|---|---|
| 3,963,649 | 6/1976 | Spadini et al. | 252/546 |
| 4,075,131 | 2/1978 | Sterling | 252/542 |
| 4,080,372 | 3/1978 | Stein et al. | 260/400 |
| 4,133,779 | 1/1979 | Hellyer et al. | 252/547 |
| 4,316,824 | 2/1982 | Pancheri | 252/551 |
| 4,421,668 | 12/1983 | Cox et al. | 252/95 X |
| 4,435,317 | 3/1984 | Gerritsen et al. | 252/551 X |
| 4,491,539 | 1/1985 | Hoskins et al. | 252/551 X |
| 4,492,646 | 1/1985 | Welch | 252/551 X |
| 4,536,317 | 8/1985 | Llenado et al. | 252/174.17 |
| 4,536,318 | 8/1985 | Cook et al. | 252/DIG. 14 |
| 4,547,318 | 10/1985 | Kloetzer et al. | 260/400 |
| 4,548,744 | 10/1985 | Connor | 252/546 X |
| 4,555,360 | 11/1985 | Bissett et al. | 252/551 X |
| 4,565,647 | 1/1986 | Llenado | 252/DIG. 14 |
| 4,566,984 | 1/1986 | Bush | 252/140 |
| 4,599,188 | 7/1986 | Llenado | 252/174.21 X |
| 4,678,606 | 7/1987 | Akhter et al. | 252/551 X |
| 4,681,704 | 7/1987 | Bernardino et al. | 252/546 |
| 4,820,447 | 4/1989 | Medcalf, Jr. et al. | 252/117 |
| 4,842,850 | 6/1989 | Vu | 252/554 X |
| 4,904,359 | 2/1990 | Pancheri et al. | 252/174.21 X |
| 4,904,406 | 2/1990 | Darwent et al. | 252/102 |
| 4,906,459 | 3/1990 | Cobb et al. | 252/550 X |
| 4,927,563 | 5/1990 | McCall | 252/551 |
| 5,021,183 | 6/1991 | Saud | 252/108 |

Primary Examiner—W. J. Shine
Assistant Examiner—Douglas J. McGinty
Attorney, Agent, or Firm—Mary P. McMahon; Kathleen M. Harleston

[57] ABSTRACT

Stable colorless detergent compositions are provided comprising anionic and/or nonionic surfactant, oxygen bleach and metal sequestering agent. The compositions do not discolor over time or under harsh temperatures.

26 Claims, No Drawings

COLORLESS DETERGENT COMPOSITIONS WITH ENHANCED STABILITY

TECHNICAL FIELD

This invention relates to stable, colorless detergent compositions containing anionic and/or nonionic surfactant, oxygen bleach and metal sequestering agent.

SUMMARY

The present invention relates to a colorless detergent composition comprising:
(a) from about 5% to about 95% by weight of anionic or nonionic surfactant;
(b) from about 0.005% to about 10% by weight of oxygen bleach; and
(c) from about 0.001% to about 8% by weight of metal sequestering agent;
wherein the composition has a pH between about 4 and about 11, and a transmittance at 470 nm. of greater than about 85%. This composition exhibits good stability over time and under harsh temperatures.

BACKGROUND INFORMATION

Detergent compositions for performing a wide variety of household and industrial cleaning operations are known in the art and are formulated for optimized performance under the contemplated end use conditions. See for example U.S. Pat. Nos. 4,555,360, Bissett et al, issued Nov. 26, 1985; 4,435,317, Gerritsen et al, issued Mar. 6, 1984; 4,681,704 Bernardino et al, issued Jul. 21, 1987; 4,316,824, Pancheri, issued Feb. 23, 1982; 4,904,359, Pancheri et al, issued Feb. 27, 1990; 4,133,779, Hellyer et al, issued Jan. 9, 1979, and 4,678,606, Akhter et al, issued Jul. 7, 1987. Along with optimized performance, a product which after storage is stable and aesthetically pleasing is desirable. It is especially difficult to achieve a stable colorless detergent composition.

It is possible to develop a clear detergent product; however, detergent ingredients such as anionic surfactants and suds boosters cause product yellowing or darkening over time. Dyes are often added to the compositions to compensate for this discoloration.

It has been found that a stable colorless detergent composition can be attained by adding certain amounts of oxygen bleach and metal sequestering agent to anionic and/or nonionic surfactant.

DESCRIPTION OF THE INVENTION

The present invention encompasses detergent compositions which are stable and remain colorless over time, even under harsh temperatures. These detergent compositions contain three essential components:
(1) from about 5% to about 95% by weight of anionic and/or nonionic surfactant;
(2) from about 0.005% to about 10% by weight of oxygen bleach; and
(3) from about 0.001% to about 8% by weight of metal sequestering agent.
Optional ingredients, especially suds boosters, can be added to provide various performance and aesthetic benefits.

These components provide a substantially colorless detergent product which does not darken or yellow under normal to harsh conditions to which a detergent composition would be exposed. Without these components, especially if anionic surfactant and suds booster are present, the product can be yellow initially and with time can become even more discolored.

Surfactant

The compositions of this invention contain from about 5% to about 95% by weight, preferably from about 10% to about 65%, most preferably from about 15% to about 35%, of an anionic and/or nonionic surfactant.

The preferred anionic surfactant is selected from the group consisting of linear alkyl benzene sulfonate having about 9 to 15 carbon atoms in the alkyl group, alkyl sulfate having about 8 to 22 carbon atoms, alkyl ether sulfate having about 8 to 22 carbon atoms in the alkyl group and about 1 to 30 ethylene oxide units, olefin sulfonate having 8 to 22 carbon atoms, alkyl glyceryl ether sulfonate having 8 to 22 carbon atoms, fatty acid ester sulfonate condensates of fatty acids with sarcosine, alkyl ethoxy carboxylate and mixtures thereof.

Preferred anionic synthetic detergents which can form the surfactant component of the compositions of the present invention are the sodium, ammonium, potassium or magnesium alkyl sulfates, especially those obtained by sulfating the higher alcohols ($C_8$–$C_{18}$ carbon atoms) sodium or magnesium alkyl benzene or alkyl toluene sulfonates, in which the alkyl group contains from about 9 to about 15 carbon atoms, the alkyl radical being either a straight or branched aliphatic chain; sodium or magnesium paraffin sulfonates ad olefin sulfonates in which the alkyl or alkenyl group contains from about 10 to about 20 carbon atoms; sodium $C_{10-20}$ alkyl glyceryl ether sulfonates, especially those ethers of alcohols derived from tallow and coconut oil; sodium coconut oil fatty acid monoglyceride sulfates and sulfonates; sodium, ammonium or magnesium salts of alkyl phenol ethylene oxide ether sulfates with about 1 to about 30 units of ethylene oxide per molecule and in which the alkyl radicals contain from 8 to about 12 carbon atoms; the reaction products of fatty acids esterified with isethionic acid and neutralized with sodium hydroxide where, for example, the fatty acids are derived from coconut oil; sodium or potassium salts of fatty acid amides of a methyl tauride in which the fatty acids, for example, are derived from coconut oil and sodium or potassium beta-acetoxy or beta-acetamido-alkanesulfonates where the alkane has from 8 to 22 carbon atoms.

Other specific examples of alkyl sulfate salts which can be employed in the instant detergent compositions include sodium lauryl alkyl sulfate, ammonium lauryl alkyl sulfate, sodium stearyl alkyl sulfate, sodium palmityl alkyl sulfate, sodium decyl sulfate, sodium myristyl alkyl sulfate, potassium lauryl alkyl sulfate, potassium stearyl alkyl sulfate, potassium decyl sulfate, potassium palmityl alkyl sulfate, potassium yristyl alkyl sulfate, sodium dodecyl sulfate, magnesium dodecyl sulfate, potassium tallow alkyl sulfate, sodium tallow alkyl sulfate, sodium coconut alkyl sulfate, potassium coconut alkyl sulfate, magnesium $C_{12-15}$ alkyl sulfate and mixtures of these surfactants. Preferred alkyl sulfates include ammonium $C_{12-15}$ alkyl sulfates and sodium $C_{12-15}$ alkyl sulfate.

Suitable alkylbenzene or alkyltoluene sulfonates include the alkali metal (lithium, sodium, potassium), alkaline earth (calcium, magnesium) ammonium and alkanolamine salts of straight or branched-chain alkylbenzene or alkyltoluene sulfonic acids. Alkylbenzene sulfonic acids useful as precursors for these surfactants include decyl benzene sulfonic acid, undecyl benzene sulfonic acid, dodecyl benzene sulfonic acid, tridecyl benzene sulfonic acid, tetrapropylene benzene sulfonic acid and mixtures thereof. Preferred sulfonic acids as precursors of the alkylbenzene sulfonates useful for compositions herein are those in which the alkyl chain is linear and averages about 11 to 13 carbon atoms in length. Examples of commercially available alkyl benzene sulfonic acids useful in the present invention include Conoco SA 515 and SA 597 marketed by the Continental Oil Company and Calsoft LAS 99 marketed by the Pilot Chemical Company.

Particularly preferred anionic surfactants useful herein are alkyl ether sulfates having eh formula $RO(C_2H_4O)_xSO_3M$ wherein R is alkyl or alkenyl of about 10 to about 20 carbon atoms, x is 1 to 30, and M is a water-soluble cation. The alkyl ether sulfates useful in the present invention are condensation products of ethylene oxide and monohydric alcohols having from about 10 to about 20 carbon atoms. Preferably, R has 10 to 16 carbon atoms. The alcohols can be derived from natural fats, e.g., coconut oil or tallow, or can be synthetic. Such alcohols are reacted with 1 to 30, and especially 1 to 12, molar proportions of ethylene oxide and the resulting mixture of molecular species is sulfated and neutralized.

Specific examples of alkyl ether sulfates of the present invention are sodium coconut alkyl triethylene glycol ether sulfate, magnesium $C_{12-15}$ alkyl triethylene glycol ether sulfate, and sodium tallow alkyl hexaoxyethylene sulfate. Preferred alkyl ether sulfates are those comprising a mixture of individual compounds, said mixture having an average alkyl chain length of from about 12 to 16 carbon atoms and an average degree of ethoxylation of from about 1 to 12 moles of ethylene oxide.

Additional examples of anionic surfactants useful herein are the compounds which contain two anionic functional groups. These are referred to as dianionic surfactants. Suitable dianionic surfactants are the disulfonates, disulfates, or mixtures thereof which may be represented by the following formula:

$$R(SO_3)_2M_2 R(SO_4)_2M_2 R(SO_3)(SO_4)M_2$$

where R is an acyclic aliphatic hydrocarbyl group having 15 to 20 carbon atoms and M is a water-solubilizing cation, for example, the $C_{15}$ to $C_{20}$ disodium 1,2-alkyldisulfates, $C_{15}$ to $C_{20}$ dipotassium-1,2-alkyldisulfonates or disulfates, di-sodium 1,9-hexadecyl disulfates, $C_{15}$ to $C_{20}$ disodium 1,2-alkyldisulfonates, disodium 1,9-stearyldisulfates and 6,10-octadecyldisulfates.

Suitable alkyl ethoxy carboxylates of the present invention have the generic formula $RO(CH_2CH_2O)_xCH_2COO-M+$ wherein R is a $C_{12}$ to $C_{16}$ alkyl group, x ranges from 0 to about 10, and the ethoxylate distribution is such that, on a weight basis, the amount of material where x is 0 is less than about 20%, preferably less than about 15%, most preferably less than about 10%, and the amount of material where x is greater than 7 is less than about 25%, preferably less than about 15%, most preferably less than about 10%, the average x is from about 2 to 4 when the average R is $C_{13}$ or less, and the average x is from about 3 to 6 when the average R is greater than $C_{13}$, and M is a cation, preferably chosen from alkali metal, alkaline earth metal, ammonium, mono-, di, and tri-ethanolammonium, most preferably from sodium, potassium, ammonium, and mixtures thereof with magnesium ions. The preferred alkyl ethoxy carboxylates are those where R is a $C_{12}$ to $C_{14}$ alkyl group.

Fatty acid ester sulfonates of the present invention are of the formula:

$$R_1-CH(SO_3^-M^+)CO_2R_2$$

wherein $R_1$ is straight or branched alkyl from about $C_8$ to $C_{18}$, preferably $C_{12}$ to $C_{16}$, and $R_2$ is straight or branched alkyl from about $C_1$ to $C_6$, preferably primarily $C_1$, and $M^+$ represents a mono- or divalent cation.

Suitable surfactants of the present invention also include the alpha-sulfonated fatty acid alkyl ester of the formula $$R_1-\underset{\underset{SO_3M}{|}}{CH}-\overset{\overset{O}{\|}}{C}-OR_2$$

wherein $R_1$ is on the average a $C_8$ to $C_{16}$, preferably a $C_{10}$ to $C_{14}$, alkyl; $R_2$ is on the average a $C_1$ to $C_6$, preferably a $C_1$ to $C_2$ alkyl; and M is a cation, preferably ammonium, sodium, potassium, magnesium, or mixtures thereof.

Particularly preferred nonionic surfactant of the present invention is selected from the group comprising alkyl polyglucoside, alcohol ethoxylated with from about 1 to 30 moles of ethylene oxide per mole of alcohol, polyhydroxy fatty acid amide, and mixtures thereof.

suitable nonionic surfactants of the present invention include the ethoxylated nonionic surfactants. These include the condensation product of alcohols, alkyl phenols and other specified hydrophobic molecules with ethylene oxide of the formula $$R(OC_2H_4)_nOH$$

wherein R is an alphatic hydrocarbyl radical containing from about 1 to about 30 carbon atoms, wherein n is from about 10 to about 100. Examples of alternate ethoxylated nonionic surfactants are:

(1) an ethoxylated alkyl phenol of the formula $R(OC_2H_4)_nOH$ wherein R is an alkyl phenyl radical containing a total of from about 18 to about 30 carbon atoms and at least one alkyl group containing at least about 12 carbon atoms wherein n is from about 16 to about 100;

(2) the condensation product of mono $C_{16-22}$ fatty acid esters of polyglycols with from about 13 to about 100 moles of ethylene oxide per mole of partial ester;

(3) the condensation product of cholesterol and from about 13 to about 100 moles of ethylene oxide;

(4) a material which is a condensate of ethylene oxide, propylene oxide and a compound containing hydroxy or amine groups onto which the alkylene oxides can be polymerized, said polymer having a molecular weight of from about 500 to about 15,000, an ethylene oxide content of from about 30% to about 70% by weight and a propylene oxide content of from about 30% to about 70% by weight.

In a particularly preferred embodiment an aliphatic alcohol contains from about 8 to about 16 carbon atoms and is ethoxylated to an average degree of from about 1 to about 30 moles of ethylene oxide per mole of alcohol.

Other useful nonionic surfactants for use in the present compositions are the nonionic alkylpolyglucosides. These surfactants contain straight chain or branched chain about C8 to C15, preferably from about C12 to C14, alkyl groups and have an average of from about 1 to 5 glucose units, with an average of 1 to 2 glucose units being most preferred. U.S. Pat. Nos. 4,393,203 and 4,732,704, incorporated by reference, describe these surfactants.

An example of another suitable surfactant of the present invention is a polymeric surfactant, preferably represented by the formula:

$$[R]_1[(R^2O)_n(R^3O)_m]_y[R^4]$$

wherein each $R_1$ is selected from the group consisting of hydrogen, alkyl groups containing from one to about 18 carbon atoms, acyl groups containing from two to about 18 carbon atoms, —SO$_4$M, —SO$_3$M, —COOM, —N(R$^5$)$_2$—O, —N(R$^5$)$_3$(+), amide groups, pyrollidone groups, saccharide groups, and hydroxy groups in which each M is a compatible cation and each $R^5$ is either an alkyl or hydroxy alkyl group containing from one to about four carbon atoms; wherein each $R^2$ or $R^3$ is an alkylene group containing from two to about six carbon atoms with no more than about 90% of said molecule comprising $R^2$ and $R^3$ groups containing two carbon atoms; wherein $R^4$ is selected from the group consisting of alkylene groups containing from one to about 18 carbon atoms and having from two to about six valences, polyhydroxyalkylene oxide groups wherein each alkylene group has from one to about six hydroxy groups and contains from three to about eight carbon atoms and there are from two to about 50 hydroxyalkylene oxide groups and from two to about 50 hydroxy groups, (═NR$^2$N═), hydrogen, ═N—(R$^2$N-H)—x, polyester groups containing from one to about 20 ester linkages and each ester group containing from about 4 to about 18 carbon atoms; wherein n is from 0 to about 500, m is for 0 to about 500, n+m is for about 5 to about 1000, x is for about 2 to about 50, and y is from 1 to about 50 and equal to the valences of R$^4$, wherein the molecular weight is from about 400 to about 60,000; and wherein the —(R$^2$O)— and the —(R$^3$O)— groups are interchangeable (as disclosed in U.S. Pat. No. 4,904,359, incorporated herein by reference).

The compositions hereof may also contain a polyhydroxy fatty acid amide surfactant of the structural formula:

(I)

wherein: $R^1$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); ad $R^2$ is a $C_5$–$C_{31}$ hydrocarbyl, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixtures thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —CH$_2$—(CHOH)$_n$—CH$_2$OH, —CH(CH$_2$OH)—(CHOH)$_{n-1}$—CH$_2$OH, —CH$_2$—(CHOH)$_2$(CHOR')(CHOH)—CH$_2$OH, where n is an integer from 3 to 5, inclusive, and R' is H or a cyclic or aliphatic monosaccharide, and alkoxylated derivatives thereof. Most preferred are glycityls wherein n is 4, particularly —CH$_2$—(CHOH)$_4$—CH$_2$OH.

In Formula (I), $R^1$ can be, for example, N-methyl, N-ethyl, N-propyl, N-isopropyl, N-butyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Methods for making polyhydroxy fatty acid amides are known in the art. In general, they can be made by reacting an alkyl amine with a reducing sugar in a reductive amination reaction to form a corresponding N-alkyl polyhydroxyamine, and then reacting the N-alkyl polyhydroxyamine with a fatty aliphatic ester or triglyceride in a condensation/amidation step to form the N-alkyl, N-polyhydroxy fatty acid amide product. Processes for making compositions containing polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

The present invention comprises any of the above described surfactants and/or mixtures thereof. Particularly preferred is anionic surfactant selected from a group consisting of linear alkyl benzene sulfonate having about 9 to 15 carbon atoms in the alkyl group, alkyl sulfate having about 8 to 22 carbon atoms, alkyl ethoxy sulfate having about 8 to 22 carbon atoms in the alkyl group and about 1 to 30 ethylene oxide units, olefin sulfonates having 8 to 22 carbon atoms, fatty acid ester sulfonate, alkyl ethoxy carboxylate, and mixtures thereof.

Oxygen Bleach

The compositions of this invention contain from about 0.005% to about 10%, preferably from about 0.01% to about 3%, most preferably from about 0.05% to about 0.5% by weight of oxygen bleach. Preferred oxygen bleaches are hydrogen peroxide, perborates, persulfates, perphosphates, periodinates, percarbonates, peroxysulfates and mixtures thereof. Most preferred is hydrogen peroxide.

The amount of oxygen bleach required will depend in part upon its strength and the strength and amount of the metal sequestering agent described hereinbelow. Preferred is a ratio of anionic and nonionic surfactant to oxygen bleach of at least about 1,500:1, preferably from about 10:1 to about 1,000:1, more preferably from about 50:1 to about 500:1, most preferably from about 100:1 to about 300:1. In addition, the composition preferably has an available oxygen (AvO) level of from about 0.005% to about 2.5%, most preferably about 0.01% to about 0.5%. Lastly, the oxygen bleach of the present invention should be compatible with detergent ingredients added to form a final product.

Metal Sequestering Agent

The compositions of this invention also contain from about 0.001% to about 8%, preferably from about 0.005% to about 5%, most preferably from about 0.01% to about 2%, by weight of a metal sequestering (chelating) agent. The preferred sequestering agent is a water-soluble, metal sequestering agent selected from the group consisting of citric acid, tartaric acid, sodium tripolyphosphate, sodium carbonate, potassium carbonate, sodium pyrophosphate, potassium phyrophosphate, potassium tripolyphosphate, sodium hexametaphosphate, bicarbonate, silicate, alkali metal polycarboxylates, e.g., sodium and potassium citrates, sodium and potassium tartrate, sodium and potassium ethylenediaminetetraacetate, sodium and potassium ethylenepentaacetate, sodium and potassium N-(2-hydroxyethyl)-ethylene diamine triacetates, sodium and potassium nitrilo triacetates (NTA), sodium and potassium N-(2-hydroxyethyl)-nitrilo diacetates, sodium and potassium oxydisuccinates, and sodium and potassium tartrate mono- and di-succinates, such as described in U.S. Pat. No. 4,663,071 (Bush et al, issued May 5, 1987), incorporated herein by reference. The sequestering agent should be environmentally acceptable. A highly preferred metal sequestering agent is citric acid and its salts, i.e. sodium, potassium and ammonium.

Without being bound by theory it is believed that yellowing and darkening of the detergent composition is prevented by the metal sequestering agent binding with metals in the composition, especially iron. Without the sequestering agent, metals will react with the oxygen bleach to form hydroxide radicals. These radicals may react with the detergent surfactant to form color bodies. Therefore, a sufficient amount of sequestering agent should be present to tie up the metals, resulting in a stable colorless detergent composition.

The Optional Suds Booster

Another component which is preferably included in the composition of this invention is an auxiliary suds booster at a level of from 1% to about 20%, preferably from about 1% to about 10%, most preferably from about 2% to about 7%. Preferred suds boosters in the instant compositions are of three basic types—betaines, amine oxide semi-polar nonionic surfactant, fatty acid amide and mixtures thereof.

The compositions of this invention can contain betaine detergent surfactants having the general formula:

$$R-N(R^1)_2{}^{(+)}-R^2COO^{(-)}$$

wherein R is a hydrophobic group selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring being treated as equivalent to about 2 carbon atoms, and similar structures interrupted by amido or ether linkages; each $R^1$ is an alkyl group containing from 1 to about 3 carbon atoms; and $R^2$ is an alkylene group containing from 1 to about 6 carbon atoms.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate.

Other suitable amidoalkylbetaines are disclosed in U.S. Pat. Nos. 3,950,417; 4,137,191; and 4,375,421; and British Patent GB No. 2,103,236, all of which are incorporated herein by reference.

It will be recognized that the alkyl (and acyl) groups for the above betaine surfactants can be derived for either natural or synthetic sources, e.g., they can be derived from naturally occurring fatty acids; olefins such as those prepared by Ziegler, or Oxo processes; or from olefins separated from petroleum either with or without "cracking".

Amine oxide semi-polar nonionic surfactants comprise compounds and mixtures of compounds having the formula $$R_1(CH_2H_4O)_n\overset{\overset{\displaystyle R_2}{|}}{\underset{\underset{\displaystyle R_3}{|}}{N}}-O$$

wherein $R_1$ is an alkyl, 2-hydroxyalkyl, 3-hydroxyalkyl, or 3-alkoxy-2-hydroxypropyl radical in which the alkyl and alkoxy, respectively, contain from about 8 to about 18 carbon atoms, $R_2$ and $R_3$ are each methyl, ethyl, propyl, isopropyl, 2-hydroxyethyl, 2-hydroxypropyl, or 3-hydroxypropyl, and n is from 0 to about 10. Particularly preferred are amine oxides of the formula:

$$R_1-\overset{\overset{\displaystyle R_2}{|}}{\underset{\underset{\displaystyle R_3}{|}}{N}}-O$$

wherein $R_1$ is a $C_{12-16}$ alkyl and $R_2$ and $R_3$ are methyl or ethyl.

Examples of the amide surfactants useful herein include the ammonia, monoethanol, and diethanol amides of fatty acids having an acyl moiety containing from about 8 to about 18 carbon atoms and represented by the general formula:

$$R_1-CO-N(H)_{m-1}(R_2OH)_{3-m}$$

wherein $R_1$ is a saturated or unsaturated, aliphatic hydrocarbon radical having from about 7 to 21, preferably from about 11 to 17 carbon atoms; $R_2$ represents a methylene or ethylene group; and m is 1, 2, or 3, preferably 1. Specific examples of said amides are mono-ethanol coconut fatty acid amide and diethanol dodecyl fatty acid amide. These acyl moieties may be derived from naturally occurring glycerides, e.g., coconut oil, palm oil, soybean oil, and tallow, but can be derived synthetically, e.g., by the oxidation of petroleum or by hydrogenation of carbon monoxide by the Fischer-Tropsch process. The monoethanolamides and diethanolamides of $C_{12}$ to $C_{14}$ fatty acids are preferred.

The above amides and amine oxides are more fully described in U.S. Pat. No. 4,316,824 (Pancheri), incorporated herein by reference. The above betaines are more fully described in U.S. Pat. No. 4,555,360, incorporated herein by reference.

The suds boosters used in the composition of this invention can contain any one or a mixture of the suds boosters listed above.

The preferred sudsing characteristics of dishwashing compositions of the invention are those which will provide the user of the product with an indication of cleaning potential in a dishwashing solution. Soils encountered in dishwashing behave like suds depressants, and the presence or absence of suds from the surface of a dishwashing solution is a convenient guide to product usage. Mixtures of anionic surfactants and suds boosting boosters, especially betaines and amine oxide semi polar nonionic surfactants, are preferably utilized in light duty liquid dishwashing detergent compositions of the invention because of their high sudsing characteristics, their suds stability in the presence of food soils, and their ability to indicate accurately an adequate level of product usage in the presence of soil.

Most preferred of the suds boosters are alkyl dimethyl amine oxides, alkyl amido propyl betaines, alkyl dimethyl betaines, alkyl dimethyl sulfo betaines, and mixtures thereof. Fatty alkyl amides are less preferred because of the poorer sudsing characteristics they provide in compositions of the invention. Yet mixtures of amides and the above amine oxides and betaines do provide sufficient sudsing benefits for the compositions.

Other Optional Ingredients

In addition to the ingredients described hereinbefore, the composition can contain other conventional ingredients, especially those associated with liquid and granular dishwashing compositions, shampoos, liquid and granular automatic dishwashing detergent and handwashing compositions, e.g. "liquid soaps" and bar soaps.

Optional ingredients which are usually used in additive levels of below about 5% include antitarnishing agents, enzymes, electrolytes, bactericides, perfumes, optical brighteners, and the like. The compositions of the present invention preferably contain no opacifiers and/or dyes because of their adverse effect on the colorlessness benefit.

The composition can also have pH regulants present. Desirably the pH of the composition in use is from about 4 to 11, preferably from about 5 to about 9, most preferably from about 6 to about 8.

Alcohols, such as ethyl alcohol and propylene glycol, and hydrotropes, such as sodium and potassium toluene sulfonate, sodium and potassium xylene sulfonate, trisodium sulfosuccinate, and related compounds (as disclosed in U.S. Pat. No. 3,915,903, incorporated herein by reference), and urea, can be utilized in the interests of achieving a desired product phase stability and viscosity. Alcohols such as ethyl alcohol and propylene glycol at a level of from 0% to about 15%, potassium or sodium toluene, xylene, or cumene sulfonate at a level of from 0% to about 10% and urea at a level of from 0% to about 10% are useful.

Other desirable ingredients include diluents and solvents. Diluents can be inorganic salts, such as sodium sulfate, ammonium chloride, sodium chloride, sodium bicarbonate, etc., and the solvents include water, lower molecular weight alcohols, such as ethyl alcohol, isopropyl alcohol, etc. Compositions herein will typically contain up to about 80%, preferably from about 30% to about 70%, most preferably from about 40% to about 65%, of water.

A light duty liquid detergent composition comprising from about 10% to about 35% of alkyl ether sulfate, from about 0.05 to about 0.05% to about 5% of hydrogen peroxide, from about 0.01% to about 2% of citric acid, ad from about 1% to about 7% of amine oxide; the composition being substantially clear and colorless and having a pH between about 5 and 9.

A shampoo composition comprising from about 1% to about 25% of ammonium lauryl sulfate and from about 0.1% to about 1% of citric acid.

Various methods can be used to prepare the detergent compositions herein described. The most preferred method for preparing a final detergent product of the present invention comprises:

(a) forming a colorless paste at a temperature of from about 70° F. to about 180° F., preferably from about 90° F. to about 130° F., the paste comprising from about 30% to about 80%, preferably from about 40% to about 70%, by weight of the paste, of antionic and nonionic surfactant; from about 0.05% to about 2%, preferably from about 0.1% to about 1%, by weight of the paste, of oxygen bleach; from about 0.005% to about 5%, by weight of the paste, of metal sequestering agent; and from about 0% to about 20%, preferably from about 5% to about 15%, of alcohol; the paste having a pH greater than about 7 and being substantially colorless; and (b) adding to the paste of step (a) sufficient ingredients to form a colorless detergent composition, which is preferably a light duty liquid dishwashing composition. Anionic surfactant, particularly alkyl sulfate having about 8 to 22 carbon atoms and alkyl ether sulfate having 8 to 22 carbon atoms in the alkyl group and about 1 to 30 ethylene oxide units, hydrogen peroxide, citric acid and ethanol or methanol are preferred. The benefit of making a stable, clear and colorless paste prior to forming the final product is that a desired final product is obtained faster and more easily than if the components were individually added. Preferred types of detergent compositions herein are light duty liquid dishwashing detergents, liquid and granular automatic dishwashing detergents, shampoos, liquid soaps, bar soaps, and liquid and granular laundry detergents.

The above described colorless paste can alternatively be used to form granules which can then be added with other standard ingredients to make granular automatic dishwashing detergents and/or granular laundry detergent ingredients. Preferably, though, the paste is diluted with ingredients for light duty liquid dishwashing detergent compositions.

Color is evaluated using % transmittance (0–100) measured by a spectrophotometer. At a wavelength of 470 nm a clear and substantially colorless product herein measures greater than about 85%, preferably greater than about 90%, most preferably greater than about 95% transmittance.

The following examples illustrate the invention and facilitate its understanding.

EXAMPLE I

A light duty liquid dishwashing detergent composition of the present invention is as follows.

TABLE 1

| Ingredient | % by weight |
| --- | --- |
| Ammonium C$_{12-13}$ alkyl ethoxy (1.0 ave.) | 15.5 |

TABLE 1-continued

| Ingredient | % by weight |
|---|---|
| sulfate | |
| Ammonium $C_{12-13}$ alkyl ethoxy (6.5 ave.) sulfate | 12.0 |
| Sodium chloride | 1.0 |
| Dodecyl dimethyl amine oxide | 5.0 |
| Ammonium xylene sulfonate | 4.0 |
| Ethanol | 5.5 |
| Perfume | 0.09 |
| Citric acid | 0.1 |
| Hydrogen peroxide | 0.18 |
| Water | Balance |
| pH = 7.1 @ 10% | |

A liquid dishwashing detergent of the above composition was filled into clear 22 oz. PET (polyethyleneterephthalate) bottles and placed in constant temperature rooms of 70° F., 90° f., 100° F., 120° F., and 140° F. After 6 months the compositions were evaluated for color stability and any signs of darkening, specifically yellowing. The product's color was evaluated on a Coleman Spectrophotometer model 295. The Coleman meter measures the % transmittance (0–100) of a chosen frequency of visible light through the product held in a standard glass sample vial. The wavelength of the light used in these measurements was 470 nm., which effectively measures the yellowing of products. The meter is calibrated to measure 100% transmittance through the standard vial when it contains distilled water. The sample vial is then filled with product and the sample's % transmittance read. Higher % transmittances are therefore preferred when the objective is to achieve colorless products. The results are as follows.

TABLE 2

Composition After 6 Months

| Temperature | % Transmittance (@ 470 nm) |
|---|---|
| 70° F. | 97 |
| 90° F. | 97 |
| 100° F. | 97.5 |
| 120° F. | 97 |
| 140° F. | 97 |

Before storage, % transmittance was about 96%. Before and after storage, the composition is nearly water-clear and colorless.

Surprisingly, the light duty detergent compositions maintained high transmittance numbers over time and temperature extremes.

EXAMPLE II

Light duty liquid dishwashing detergent compositions of the present invention are as follows. The % transmittance test is performed as described in Example I with the samples being measured at 17 days. The results are set forth in Table 3.

TABLE 3

| Ingredient | A | B | C | D | E | F | G | H |
|---|---|---|---|---|---|---|---|---|
| Ammonium $C_{12-13}$ alkyl ethoxy (1.0 ave) sulfate | 15.5 | 15.5 | 15.5 | 15.5 | 15.5 | 15.5 | 15.5 | 15.5 |
| Ammonium $C_{12-13}$ alkyl ethoxy (6.5 ave) sulfate | 12.0 | 12.0 | 12.0 | 12.0 | 12.0 | 12.0 | 12.0 | 12.0 |
| Sodium chloride | 1.0 | 1.0 | 1.0 | 1.0 | 1.0 | 1.0 | 1.0 | 1.0 |
| Ammonium xylene sulfonate | 4.0 | 4.0 | 4.0 | 4.0 | 4.0 | 4.0 | 4.0 | 4.0 |
| Ethanol | 5.5 | 5.5 | 5.5 | 5.5 | 5.5 | 5.5 | 5.5 | 5.5 |
| Perfume | 0.09 | 0.09 | 0.09 | 0.09 | 0.09 | 0.09 | 0.09 | 0.09 |
| Dodecyl dimethyl amine oxide | 0.0 | 0.0 | 0.0 | 0.0 | 5.0 | 5.0 | 5.0 | 5.0 |
| Citric acid | 0.0 | 0.0 | 0.1 | 0.1 | 0.1 | 0.0 | 0.1 | 0.0 |
| Hydrogen peroxide | 0.0 | 0.18 | 0.0 | 0.18 | 0.18 | 0.0 | 0.0 | 0.18 |
| Water | Balance | | | | | | | |

A pH of 7.1@10% is obtained by using pH trim.

| | | | | | | | | |
|---|---|---|---|---|---|---|---|---|
| % transmittance (@ 470 nm) | 90 | 92 | 85 | 96 | 93 | 66 | 82 | 43 |

Surprisingly, superior color stability results are attained when both hydrogen peroxide and citric acid (Samples D and E) are used. Hydrogen peroxide alone (Sample B), especially with amine oxide in the composition (Sample H), is not as colorless as when both hydrogen peroxide and citric acid are added. Citric acid alone (Sample C), and with amine oxide (Sample G) is not as colorless as when both hydrogen peroxide and citric acid are added.

EXAMPLE III

Anionic paste detergent compositions of the present invention are as follows. It can be seen that hydrogen peroxide alone is not sufficient to give the desired stability. The addition of hydrogen peroxide and sequestering agent (Sample B) is necessary to maintain the desired colorlessness through the end of the first day at 180° F., which is a very extreme condition (worst case). The results are set forth in Table 4.

TABLE 4

| Ingredient | A | B | C | D |
|---|---|---|---|---|
| Ammonium $C_{12-13}$ alkyl ethoxy (1.0 ave.) sulfate | 38.4 | 38.4 | 38.4 | 38.4 |
| Ammonium $C_{12-13}$ alkyl ethoxy (6.5 ave.) sulfate | 29.6 | 29.6 | 29.6 | 29.6 |
| $C_{12-13}$ alkyl ethoxy (6.5 ave) alcohol | 0.0 | 0.0 | 2.0 | 0.0 |
| Ethanol | 12.0 | 12.0 | 12.0 | 12.0 |
| Citric acid | 0.0 | 0.2 | 0.0 | 0.0 |
| Hydrogen peroxide | 0.4 | 0.4 | 0.4 | 0.0 |
| Water | Balance | | | |
| A pH of 7.8 @ 10% is obtained by using pH trim. | | | | |
| % transmittance (@ 470 nm) | | | | |
| Initial | 94 | 94 | 94 | 94 |
| 1 day | 87 | 96 | 91 | — |
| 6 days | 25 | 79 | — | 78 |

The sample with both hydrogen peroxide and citric acid (B) has the highest % transmittance (96) even after a day at 180° F. It is not expected that product will realistically ever be exposed to more than one day at 180° F.

EXAMPLE IV

A shampoo composition is as follows:

TABLE 5

| Ingredient | % by weight |
|---|---|
| Ammonium lauryl sulfate | 10 |
| Ammonium laureth (3 ave) sulfate | 10 |
| Sodium lauroyl sarcosinate | 5 |
| Cocoamidopropyl betaine | 5 |
| Citric acid | 0.4 |
| Sodium citrate | 0.4 |
| Hydantoin | 0.2 |
| Sodium chloride | 0.5 |
| Perfume | 0.4 |
| Hydrogen peroxide | 0.15 |
| Hydroxypropyl methyl cellulose | 1.0 |
| | Balance |

EXAMPLE V

A light duty liquid detergent composition of the present invention is as follows.

TABLE 6

| Ingredient | % by weight |
|---|---|
| Ammonium $C_{12-13}$ alkyl ethoxy (1.0 ave.) sulfate | 28.5 |
| Tetronic ® 704 | 0.1 |
| Cocamidopropylbetaine | 0.9 |
| Magnesium chloride | 3.3 |
| Dodecyl dimethyl amine oxide | 2.6 |
| Ammonium xylene sulfonate | 3.0 |
| Ethanol | 4.0 |
| Perfume | 0.18 |
| Sodium diethylenepentaacetate | 0.1 |
| Hydrogen peroxide | 0.17 |
| Water | Balance |
| pH = 7.1 @ 10% | |

EXAMPLE VI

Liquid soap compositions of the present invention are as follows.

TABLE 7

| Ingredient | % by weight A | B | C |
|---|---|---|---|
| Sodium $C_{12-13}$ alkyl sulfate | 8 | 9 | — |
| Sodium $C_{12-13}$ $(EO)_2$ alkyl sulphate | 12 | — | — |
| Sodium $C_{12-13}$ $(EO)_3$ alkyl sulphate | — | 11 | — |
| Ammonium $C_{12-13}$ $(EO)_3$ alkyl sulphate | — | — | 20 |
| Commercial $C_{10}$ alcohol $(EO)_{10}$ | 4 | 2 | 2 |
| Dodecyl dimethyl amine oxide | — | — | 3 |
| Thickener (Jaguar HP-60) | 0.4 | 0.6 | 0.55 |
| Propylene glycol | 2 | — | — |
| Polyoxyethylene/polyoxypropylene block copolymer (Pluronic L-92) ® | — | — | 0.5 |
| Polyoxyethylene glycol 600 | 2 | 4 | 0 |
| Coconut monoethanolamide | 2 | 2 | — |
| Ethyleneglycol distearate | 1 | 1 | 0.5 |
| Perfume | 4 | 3 | 2 |
| Preservative[1] | 0.3 | 0.4 | 0.25 |
| Citric acid | 0.2 | 0.3 | 0.3 |
| Magnesium chloride - $6H_2O$ | — | — | — |
| Hydrogen peroxide | 0.15 | 0.15 | 0.015 |

[1] Comprises Germal 115, Methyl paraben, Propyl paraben and ethylenediamine tetraacetic acid.

What is claimed is:

1. A stable, colorless detergent composition comprising:
   (a) from about 5% to about 95% by weight of anionic or nonionic surfactant;
   (b) from about 0.005% to about 10% by weight of oxygen bleach;
   (c) from about 0.001% to about 8% by weight of metal sequestering agent; and
   (d) from about 1% to about 20% by weight of suds booster; wherein the composition has a pH between about 4 and about 11, and a transmittance at 470 nm. of greater than about 85%.

2. A method of making a colorless detergent composition comprising the steps of:
   (a) forming a paste at a temperature of from about 70° F. to about 180° F., the paste comprising from about 30% to about 80%, by weight of the paste, of anionic and nonionic surfactant; from about 0.05% to about 2%, by weight of the paste, of oxygen bleach; from about 0.005% to about 5%, by weight of the paste, of metal sequestering agent; from about 0% to about 20%, by weight of the paste, of alcohol; and from about 1% to about 20% by weight suds booster; the paste having a pH greater than about 7 and being substantially colorless; and
   (b) adding to the paste of step (a) sufficient ingredients to form a colorless detergent composition.

3. The composition of claim 1 wherein the anionic or nonionic surfactant is selected from the group consisting of linear alkyl benzene sulfonate having about 9 to 15 carbon atoms in the alkyl group, alkyl sulfate having about 8 to 22 carbon atoms, alkyl ether sulfate having about 8 to 22 carbon atoms in the alkyl group and about 1 to 30 ethylene oxide units, olefin sulfonates having 8 to 22 carbon atoms, fatty acid ester sulfonate, condensates of fatty acids with sarcosine, alkyl ethoxy carboxylate, alkyl glyceryl ether sulfonates having 8 to 22 carbon atoms, alkyl polyglucoside, alcohol ethoxylated with from about 1 to 30 moles of ethylene oxide per mole of alcohol, polyhydroxy fatty acid amide, and mixtures thereof.

4. The composition of claim 3 wherein the metal sequestering agent is selected from the group consisting of citric acid, tartaric acid, sodium tripolyphosphate, sodium carbonate, potassium carbonate, sodium pyrophosphate, potassium pyrophosphate, sodium hexametaphosphate, alkali metal polycarbonates, bicarbonate, silicate, and mixtures thereof.

5. The composition of claim 4 wherein the ratio of anionic and nonionic surfactant to oxygen bleach is at least about 1,500:1.

6. The composition of claim 5 wherein the oxygen bleach is selected from the group consisting of hydrogen peroxide, perborates, persulfates, peroxysulphates, perphosphates, periodinates, percarbonates and mixtures thereof.

7. The composition of claim 6 wherein the metal sequestering agent is citric acid.

8. The composition of claim 7 wherein the suds booster is selected from the group consisting of betaine, amine oxide semi-polar nonionic, fatty acid amide, and mixtures thereof.

9. The composition of claim 8 wherein the oxygen bleach is hydrogen peroxide.

10. The composition of claim 9 wherein the stable colorless detergent composition is selected from the group consisting of liquid and granular dishwashing detergents, liquid and granular automatic dishwashing detergents, shampoos, liquid soaps, bar soaps, and liquid and granular laundry detergents.

11. The composition of claim 10 wherein an anionic surfactant is selected from the group consisting of linear alkyl benzene sulfonate having about 9 to 15 carbon atoms in the alkyl group, alkyl sulfate having about 8 to 22 carbon atoms, alkyl ether sulfate having about 8 to 22 carbon atoms in the alkyl group and about 1 to 30 ethylene oxide units, olefin sulfonates having 8 to 22 carbon atoms, fatty acid ester sulfonate, alkyl ethoxy carboxylate, and mixtures thereof.

12. The composition of claim 11 comprising from about 0.005% to about 5% of metal sequestering agent.

13. The composition of claim 12 comprising from about 0.01% to about 3% of oxygen bleach.

14. The composition of claim 13 comprising from about 10% to about 65% of the anionic surfactant.

15. A colorless shampoo composition according to claim 14 comprising from about 1% to about 25% of ammonium lauryl sulfate and from about 0.1% to about 1% of citric acid.

16. The composition of claim 14 comprising from about 0.01% to about 2% of the metal sequestering agent.

17. The composition of claim 16 comprising from about 0.05% to about 0.5% of hydrogen peroxide and wherein the ratio of anionic and nonionic surfactant to oxygen bleach is from about 50:1 to about 500:1.

18. The composition of claim 17 wherein the transmittance at 470 nm is greater than about 90%.

19. The composition of claim 18 wherein the composition has an available oxygen level of from about 0.005% to about 2.5%.

20. A colorless detergent paste according to claim 17 comprising from about 30% to about 80% of alkyl sulfate and alkyl ether sulfate, from about 0.1% to about 1.0% of hydrogen peroxide, and from about 0.005% to about 5% of citric acid; the paste being substantially clear and colorless.

21. A light duty liquid dishwashing detergent according to claim 18 comprising from about 10% to about 35% of alkyl ether sulfate, from about 0.05% to about 5% of hydrogen peroxide, from about 0.01% to about 2% of citric acid, and from about 1% to about 7% of amine oxide; the composition being substantially clear and colorless and having a pH between about 5 and 9.

22. The method of claim 2 wherein the colorless detergent composition is a light duty liquid dishwashing composition.

23. The method of claim 22 wherein the paste of step (a) comprises from about 40% to about 70%, by weight of the paste, of anionic surfactant; from about 0.1% to about 1%, by weight of the paste, of oxygen bleach; from about 0.01% to about 2%, by weight of the paste, of metal sequestering agent; and from about 1% to about 10%, by weight of the paste, of alcohol.

24. The method of claim 23 wherein the oxygen bleach is hydrogen peroxide.

25. The method of claim 24 wherein the anionic surfactant is alkyl sulfate having about 8 to 22 carbon atoms and alkyl ether sulfate having 8 to 22 carbon atoms in the alkyl group and about 1 to 30 ethylene oxide units, the metal sequestering agent is citric acid, and the alcohol is ethanol or methanol.

26. The composition of claim 17 wherein the metal sequestering agent is selected from the group consisting of sodium and potassium citrates, sodium and potassium tartrate, sodium and potassium ethylenediaminetetraacetate, sodium and potassium ethylenepentaacetate, sodium and potassium N-(2-hydroxyethyl)-ethylene diamine triacetates, sodium, and potassium nitriol triacetates, sodium and potassium N-(2-hydroxyethyl)-nitrilo diacetates, sodium and potassium oxydisuccinates, sodium and potassium tartrate mono- and disuccinates and mixtures thereof.

* * * * *